United States Patent
Danilevicius et al.

(10) Patent No.: US 7,189,483 B2
(45) Date of Patent: Mar. 13, 2007

(54) CHARGE TRANSPORT MATERIALS HAVING HETEROAROMATIC HYDRAZONE GROUPS

(75) Inventors: Almantas Danilevicius, Kaunas (LT);
Gintaras Buika, Kuanas (LT);
Ramunas Lygaitis, Kaunas (LT);
Juozas V. Grazulevicius, Kaunas (LT);
Robertas Maldzius, Vilnius (LT);
Edmundas Montrimas, Vilnius (LT);
Zbigniew Tokarski, Woodbury, MN (US); Nusrallah Jubran, St. Paul, MN (US)

(73) Assignee: Samsung Electronics Co., Ltd., Suwon (KR)

( * ) Notice: Subject to any disclaimer, the term of this patent is extended or adjusted under 35 U.S.C. 154(b) by 347 days.

(21) Appl. No.: 10/789,094

(22) Filed: Feb. 27, 2004

(65) Prior Publication Data

US 2004/0241563 A1   Dec. 2, 2004

Related U.S. Application Data

(60) Provisional application No. 60/474,542, filed on May 30, 2003.

(51) Int. Cl.
*G03G 5/047* (2006.01)
(52) U.S. Cl. .................... 430/76; 430/77; 430/78; 544/42; 544/73; 544/347
(58) Field of Classification Search ............ 430/76, 430/77, 78; 544/42, 73, 347
See application file for complete search history.

(56) References Cited

U.S. PATENT DOCUMENTS

| | | | |
|---|---|---|---|
| 4,297,426 A | 10/1981 | Sakai et al. | |
| 4,403,025 A | 9/1983 | Horie et al. | |
| 4,477,550 A | 10/1984 | Horie et al. | |
| 4,786,571 A | 11/1988 | Ueda | |
| 4,957,838 A | 9/1990 | Aruga et al. | |
| 5,089,366 A | 2/1992 | Haino et al. | |
| 5,128,227 A | 7/1992 | Monbaliu et al. | |
| 5,942,615 A | 8/1999 | Kobayashi et al. | |
| 6,066,426 A | 5/2000 | Mott et al. | |
| 6,099,996 A | 8/2000 | Yanus et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,350,553 B2 | 2/2002 | Srinivasan | |
| 6,472,514 B2 | 10/2002 | Kuroda | |
| 6,670,085 B2 | 12/2003 | Jubran et al. | |
| 6,689,523 B2 | 2/2004 | Law et al. | |
| 6,696,209 B2 | 2/2004 | Law et al. | |
| 2003/0104294 A1 | 6/2003 | Law et al. | |
| 2003/0113132 A1 | 6/2003 | Law et al. | |
| 2003/0113643 A1* | 6/2003 | Law et al. | 430/58.15 |
| 2003/0113644 A1 | 6/2003 | Law et al. | |
| 2003/0138712 A1 | 7/2003 | Law et al. | |
| 2003/0198880 A1 | 10/2003 | Law et al. | |
| 2003/0219662 A1 | 11/2003 | Jubran et al. | |

FOREIGN PATENT DOCUMENTS

| | | |
|---|---|---|
| EP | 1 418 469 | 5/2004 |
| JP | 57-189142 | 11/1982 |
| JP | 09-043879 | 2/1997 |

OTHER PUBLICATIONS

Dong Hoon Choi, "Diffraction Behaviour of Photorefractive Molecular Materials Containing Phenothiazone Derivatives," Applied Physics Letters, vol. 81 (25), pp. 4727-4729 (2002).

* cited by examiner

*Primary Examiner*—Mark A. Chapman
(74) *Attorney, Agent, or Firm*—Patterson, Thuente, Skaar & Christensen, P.A.

(57) ABSTRACT

An improved organophotoreceptor includes an electrically conductive substrate and a photoconductive element on the electrically conductive substrate where the photoconductive element comprises:
a) a charge transport material having the following formula:

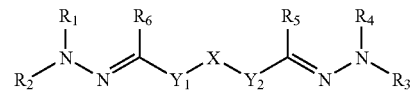

where X is a linking group;
$Y_1$ and $Y_2$ are, each independently, a phenothiazine group, a phenoxazine group, or a phenazine group;
$R_1$, $R_2$, $R_3$, and $R_4$ are, each independently, an alkyl group, an alkenyl group, a heterocyclic group, or an aromatic group; and
$R_5$ and $R_6$ are, each independently, a hydrogen, an alkyl group, an alkenyl group, a heterocyclic group, or an aromatic group; and
(b) a charge generating compound.

Corresponding electrophotographic apparatuses and imaging methods are described.

29 Claims, No Drawings

CHARGE TRANSPORT MATERIALS HAVING HETEROAROMATIC HYDRAZONE GROUPS

CROSS REFERENCE TO RELATED APPLICATION

This application claims priority to copending U.S. Provisional Patent Application Ser. No. 60/474,542 to Danilevicius et al., filed on May 30, 2003, and entitled "Novel Charge Transport Compounds," incorporated herein by reference.

FIELD OF INVENTION

This invention relates to organophotoreceptors suitable for use in electrophotography and, more specifically, to an organophotoreceptor having charge transport materials comprising at least two heteroaromatic hydrazone groups, each of which is selected from the group consisting of a phenothiazine hydrazone group, a phenoxazine hydrazone group, and a phenazine hydrazone group.

BACKGROUND

In electrophotography, an organophotoreceptor in the form of a plate, disk, sheet, belt, drum or the like having an electrically insulating photoconductive element on an electrically conductive substrate is imaged by first uniformly electrostatically charging the surface of a photoconductive element, and then exposing the charged surface to a pattern of light. The light exposure selectively dissipates the charge in the illuminated areas where light strikes the surface, thereby forming a pattern of charged and uncharged areas referred to as a latent image. A liquid toner or solid toner can then be provided in the vicinity of the latent image, and toner droplets or particles can be deposited in either the charged or uncharged areas depending on the properties of the toner to create a toned image on the surface of the photoconductive element. The resulting toned image can be transferred to a suitable ultimate or intermediate receiving surface, such as paper, or the photoconductive element can operate as the ultimate receptor for the image. The imaging process can be repeated many times to complete a single image, which can involve, for example, overlying images of distinct color components or effecting shadow images to complete a full color complete image, and/or to reproduce additional images.

Both single layer and multilayer photoconductive elements have been used. In the single layer embodiment, charge generating compound and a charge transport material selected from the group consisting of a charge transport compound, an electron transport compound, and a combination of both are combined with a polymeric binder and then deposited on the electrically conductive substrate. In the multilayer embodiments based on a charge transport compound, the charge transport compound and charge generating compound are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept these charge carriers and transport them through the charge transport layer in order to discharge a surface charge on the photoconductive element. The charge transport material can be a charge transport compound, an electron transport compound, or a combination of both. When a charge transport compound is used, the charge transport compound accepts the hole carriers and transports them through the layer in which the charge transport compound is located. When an electron transport compound is used, the electron transport compound accepts the electron carriers and transports them through the layer in which the electron transport compound is located.

SUMMARY OF THE INVENTION

This invention provides organophotoreceptors having good electrostatic properties such as high $V_{acc}$ and low $V_{dis}$.

In a first aspect, the invention pertains to an organophotoreceptor comprising an electrically conductive substrate and a photoconductive element on the electrically conductive substrate, the photoconductive element comprising:

a) a charge transport material having the following formula:

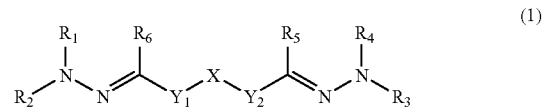

(1)

where X is a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$Y_1$ and $Y_2$ are, each independently, a phenothiazine group, a phenoxazine group, or a phenazine group;

$R_1$, $R_2$, $R_3$, and $R_4$ are, each independently, an alkyl group, an alkenyl group, a heterocyclic group, or an aromatic group; and $R_5$ and $R_6$ are, each independently, a hydrogen, an alkyl group, an alkenyl group, a heterocyclic group, or an aromatic group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, optionally a second charge transport material, and optionally a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser. The method of electrophotographic imaging with photoreceptors containing the above noted charge transport material is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having Formula (1) above.

The invention provides suitable charge transport materials for organophotoreceptors featuring a combination of good mechanical, electrostatic, and solubility properties. These photoreceptors can be used successfully with toners, such as liquid toners and dry toners, to produce high quality images. The high quality of the imaging system can be maintained after repeated cycling.

Other features and advantages of the invention will be apparent from the following description of the specific embodiments thereof, and from the claims.

DETAILED DESCRIPTION

An organophotoreceptor as described herein has an electrically conductive substrate and a photoconductive element comprising a charge generating compound and a charge transport material having two heteroaromatic hydrazone groups bonded together through a linking group. Each of the heteroaromatic hydrazone group is selected from the group consisting of a phenothiazine hydrazone group, a phenoxazine hydrazone group, and a phenazine hydrazone group. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene] anthrone, and 1-cyano-10-[bis (ethoxycarbonyl)methylene]anthrone, 7-nitro-2-aza-9-fluorenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232,800, 4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge and, in particular, holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula

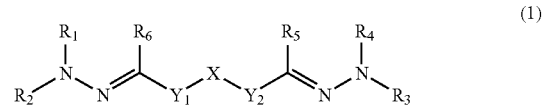

where X is a linking group, such as a $-(CH_2)_m-$ group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$Y_1$ and $Y_2$ are, each independently, a phenothiazine group, a phenoxazine group, or a phenazine group;

$R_1$, $R_2$, $R_3$, and $R_4$ are, each independently, an alkyl group, an alkenyl group, a heterocyclic group, or an aromatic group; and $R_5$ and $R_6$ are, each independently, a hydrogen, an alkyl group, an alkenyl group, a heterocyclic group, or an aromatic group.

In some embodiments of the organophotoreceptor of this invention, the charge transport material has the formula:

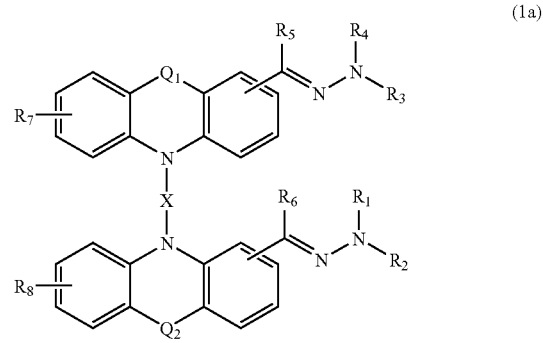

where $Q_1$ and $Q_2$ are, independently, S, O, or $NR_9$ where $R_9$ is a hydrogen, an alkyl group, an alkenyl group, a heterocyclic group, or an aromatic group;

$R_1$, $R_2$, $R_3$, and $R_4$ are, each independently, an alkyl group, an alkenyl group, a heterocyclic group, or an aromatic group;

$R_5$ and $R_6$, each independently, a hydrogen, an alkyl group, an alkenyl group, a heterocyclic group, or an aromatic group;

$R_7$ and $R_8$ are, each independently, a hydrogen, a nitro group, a cyano group, a halogen, an alkoxy group, a hydroxyl group, a thiol group, an amino group, a carboxyl group, an alkyl group, an alkenyl group, a heterocyclic group, or an aromatic group; and X is a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, Si, and N. Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, Si, and N.

Substitution is liberally allowed on the chemical groups to affect various physical effects on the properties of the compounds, such as mobility, sensitivity, solubility, compatibility, stability, and the like, as is known generally in the art. In the description of chemical substituents, there are certain practices common to the art that are reflected in the use of language. The term group indicates that the generically recited chemical entity (e.g., alkyl group, alkenyl group, aromatic group, phenothiazine group, phenoxazine group, or phenazine group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom, such as 3-ethoxylpropyl, 4-(N, N-diethylamino)butyl, 3-hydroxypentyl, 2-thiolhexyl, 1,2,3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N,N-disubstituted)aminophenyl, 2,4-dihydroxyphenyl, 2,4,6-trithiophenyl, 2,4,6-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical moiety is not substituted. When referring to an alkyl moiety, the term represents only an unsubstituted alkyl hydrocarbon group, whether branched, straight chain, or cyclic.

The charge transport material may or may not be symmetrical. Thus, for example, $R_7$ and $R_8$ groups in Formula (1a) may be the same or different; $R_6$ and $R_5$ groups in Formulae (1) and (1a) may be the same or different; Q1 and Q2 groups in Formula (1a) may be the same or different, and $R_1$, $R_2$, $R_3$, and $R_4$ groups Formulae (1) and (1a) may be the same or different. In addition, the above-described formula for the charge transport material is intended to cover isomers.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (Tedlar®, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodine, conductive polymers such as polypyrroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers (such as a dye or pigment). Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

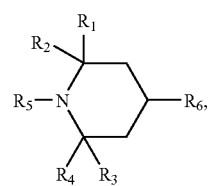

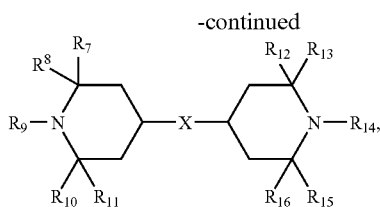

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optional additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport compound can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, poly(methyl methacrylate), poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics, and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

As described herein, an organophotoreceptor comprises a charge transport material having the formula

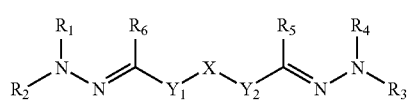

where X is a linking group, such as a —(CH$_2$)$_m$— group, where m is an integer between 1 and 30, inclusive, and one or more of the methylene groups is optionally replaced by O, S, N, C, B, Si, P, C=O, O=S=O, a heterocyclic group, an aromatic group, an NR$_a$ group, a CR$_b$ group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

Y$_1$ and Y$_2$ are, each independently, a phenothiazine group, a phenoxazine group, or a phenazine group;

R$_1$, R$_2$, R$_3$, and R$_4$ are, each independently, an alkyl group, an alkenyl group, a heterocyclic group, or an aromatic group; and R$_5$ and R$_6$ are, each independently, a hydrogen, an alkyl group, an alkenyl group, a heterocyclic group, or an aromatic group.

With respect to Formula (1), substitution is liberally allowed, especially on Y$_1$ and Y$_2$. Variation of the substituents, such as an aromatic group, an alkyl group, a heterocyclic group, and a ring group such as a benzo group, on those groups can result in various physical effects on the properties of the compounds, such as mobility, solubility, compatibility, stability, spectral absorbance, dispersibility, and the like, including, for example, substitutions known in the art to effect particular modifications.

In some embodiments, the organophotoreceptors as described herein can comprise an improved charge transport material having two heteroaromatic hydrazone groups, each of which is selected from the group consisting of a phenothiazine hydrazone group, a phenoxazine hydrazone group, and a phenazine hydrazone group. Non-limiting examples of such charge transport materials have the following formulas:

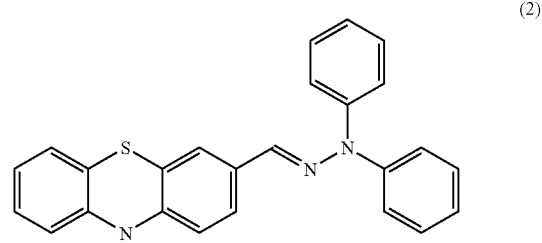

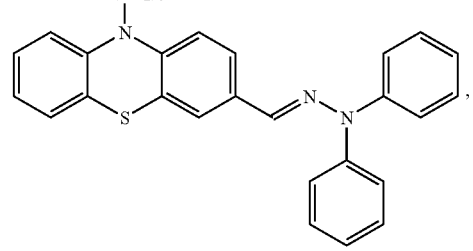

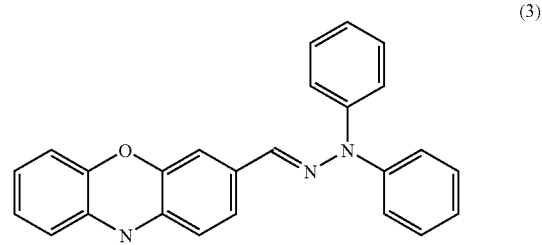

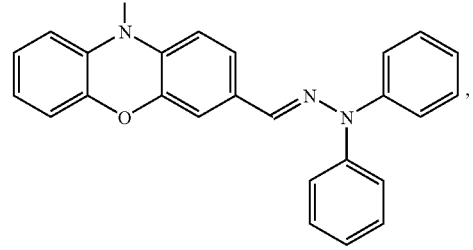

17

-continued

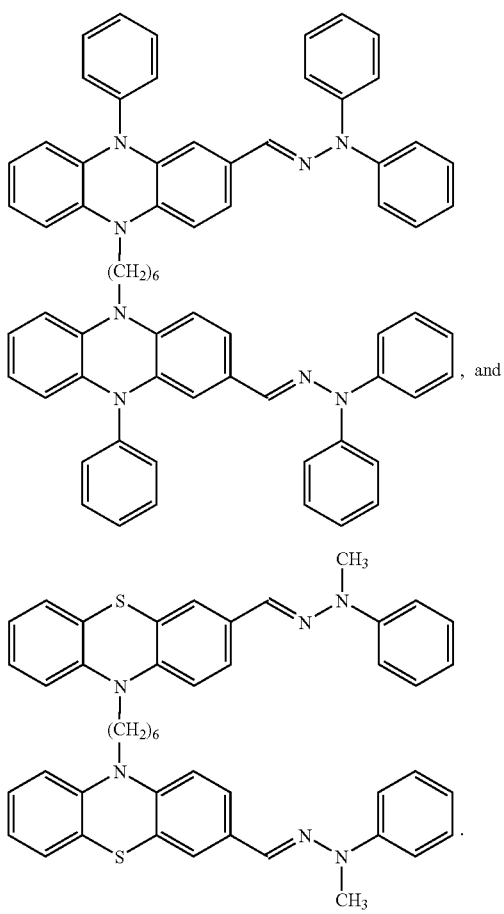

These photoreceptors can be used successfully with toners, such as liquid toners and dry toners, to produce high quality images. The high quality of the images can be maintained after repeated cycling.

General Synthesis Of Charge Transport Materials

Charge transport materials of this invention can be prepared by the following multi-step synthesis. A person of ordinary skill in the art will recognize that alternative synthesis approaches can be used based on the teaching of the synthesis described herein. The multi-step synthesis includes the following 3 steps, which may or may not be performed in this order:

1) Preparation of a heteroaromatic dimer by linking two heteroaromatic compounds selected from the group consisting of a phenothiazine compound, a phenoxazine compound, and a phenazine compound by a linking compound;
2) Preparation of a diformyl compound by diformylation of the heteroaromatic dimer;
3) Preparation of a heteroaromatic hydrazone by the condensation reaction of the diformyl compound with at least one hydrazine compound.

Step 1. Preparation of Heteroaromatic Dimer

A mixture of a heteroaromatic compound (such as a phenothiazine compound, a phenoxazine compound, and a phenazine compound), a compound having two halogen groups, an alkaline hydroxide, and a phase transfer catalyst in appropriate solvent is stirred and refluxed for an appropriate period of time. Then, the reaction mixture is cooled, filtered, and washed thoroughly with water. The organic phase is dried over anhydrous sodium sulfate. The solvent in the dried organic phase is removed by evaporation and the crude product is purified by column chromatography.

In some embodiments, the heteroaromatic compound has the general formula:

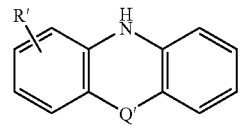

where Q' is S, O, or $NR_9$ where $R_9$ is a hydrogen, an alkyl group, an alkenyl group, a heterocyclic group, or an aromatic group and R' corresponds to one or more optional substituents.

Substitution is liberally allowed on the formula above. On the heteroaromatic ring, there may be one or more substituents, such as a nitro group, a cyano group, a halogen, an alkoxy group, a hydroxyl group, a thiol group, an amino group, a carboxyl group, an alkyl group, an alkenyl group, a heterocyclic group, an aromatic group, or a ring group such as a benzo group.

In some embodiments, the compound having two halogen groups has the formula:

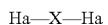

where X is a linking group, such as a $—(CH_2)_m—$ group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and Ha is Cl, Br or I. This X group corresponds with the X group of the Formula (1) following the completion of the sysnthesis.

The alkaline hydroxide can be, for example, either potassium hydroxide or sodium hydroxide. The phase transfer catalyst can be, for example, a tetra-n-butyl ammonium salt, such as tetra-n-butyl ammonium hydrogen sulfate or tetra-n-butyl ammonium bromide. The solvent can be, for example, an aromatic solvent, such as toluene or xylene.

The above procedure results in a symmetric heteroaromatic dimer. To form an asymmetric heteroaromatic dimer, two different heteroaromatic compounds are used in the synthesis. These can be reacted simultaneously or sequentially with the compound having two halogen atoms. The concentrations, reaction times and other reaction parameters can be selected by a person of skill in the art to favor formation of the asymmetric product over the symmetric product. Furthermore, the desired asymmetric product can be purified away from the symmetric products to have a purified asymmetric product for completion of the synthesis process.

Step 2. Diformylation of Heteroaromatic Dimer

In the next step, dry dimethylformamide (DMF) is added to a round-bottom flask. Then, phosphorus oxychloride, $POCl_3$, is added to the flask at 0° C. under nitrogen, followed by a solution of the heteroaromatic dimer prepared in step 1 in dry DMF. The reaction mixture is stirred at 70° C. until there is no change in the composition of the reaction mixture by thin layer chromatography (TLC). The reaction mixture is cooled to room temperature, and poured into ice water. The mixture is neutralized with potassium hydroxide (KOH) until the pH reaches 7–8, and the aqueous solution is extracted with chloroform several times. The chloroform solution is washed with water, dried with anhydrous sodium sulfate, and filtered. The solvent is removed by evaporation, and the crude product, a diformyl derivative of the heteroaromatic dimer, is purified by column chromatography. Other reactants with an oxo substituent on an amine group, such as alkylamides or arylamides, can be substituted for the dimethylformamide to yield a product of Formula (1) with a non-hydrogen group for $R_5$ and or $R_6$. To have $R_5$ different from $R_6$, two different reactants are reacted sequentially or simultaneously with the heteroaromatic dimer.

Step 3. Preparation of Heteroaromatic Hydrazone

A solution of a hydrazine compound in methanol is added dropwise to a solution of the diformyl derivative of the heteroaromatic dimer obtained in Step 2 in methanol. The hydrazine generally has the desired substituents to form the $R_1$, $R_2$, $R_3$, and $R_4$ substituents of Formula (1). The mixture is stirred and refluxed until there is no change in the composition of the reaction mixture as indicated by TLC. The reaction mixture is cooled to room temperature and the crude product is isolated and purified by recrystalization or/and by column chromatography.

The invention will now be described further by way of the following examples.

EXAMPLES

Example 1

Synthesis And Characterization of Charge Transport Materials

This example describes the synthesis and characterization of Compounds (2)–(5), in which the numbers refer to formula numbers above. The characterization involves chemical characterization of the compounds. The electrostatic characterization, such as mobility and ionization potential, of the materials formed with the compounds is presented in a subsequent example.

Compound (2)

A mixture of phenothiazine (0.15 mol), 0.1 mol of 1,6-dibromohexane, 0.15 mol of potassium hydroxide and 1% w/w of tetra-n-butyl ammonium hydrogen sulfate in 300 ml of dry toluene was stirred and refluxed for 48 hours. The reaction mixture was cooled to room temperature, filtered, and washed thoroughly with water. The organic phase was dried over anhydrous sodium sulfate, and the solvent was removed by evaporation. The crude product was purified by column chromatography using a mixture of ethyl acetate and hexane in a volume ratio of 1:6 as eluent. The yield of 1,6-di(10H-10-phenothiazinyl)hexane was 85%. The $^1$H-NMR spectrum of the product in $CDCl_3$ was characterized by the following chemical shifts ($\delta$, ppm): 1.35–1.50(m, 4H), 1.55–1.90(m, 4H), 3.82(t, 4H), and 6.73–7.19(m, 16H).

Phosphorus oxychloride was added dropwise to dry dimethylformamide (1:1.2 molar ratio) at 0° C. under nitrogen. A solution of 1,6-di(10H-10-phenothiazinyl)hexane (obtained in the previous step) in dry DMF was added stepwise to the reaction flask. The reaction mixture was stirred at 70° C. until the starting compound reacted completely as indicated by TLC. The reaction mixture was cooled to room temperature, poured into ice water, and neutralized with a dilute KOH solution until the pH reached 7–8. The aqueous solution was extracted several times with chloroform. The combined chloroform solutions were washed with water, dried with anhydrous sodium sulfate, and filtered. The solvent was removed by distillation. The crude product was purified by column chromatography using a mixture of ethyl acetate and hexane in a volume ratio of 1:8 as the eluent. The yield of 10-[6-(3-formyl-10H-10-phenothiazinyl)hexyl]-10H-3-phenothiazine carbaldehyde) was 56%. The $^1$H-NMR spectrum of the product in $CDCl_3$ was characterized by the following chemical shifts ($\delta$, ppm): 1.35–1.50 (m, 4H), 1.55–1.90 (m, 4H), 3.82 (t, 4H), 6.73–7.19 (m, 14H), and 9.80 (s, 2H).

A solution of N,N-diphenylhydrazine hydrochloride (4 moles) in methanol was added dropwise to a solution of 10-[6-(3-formyl-10H-10-phenothiazinyl)hexyl]-10H-3-phenothiazinecarbaldehyde (1 mole, obtained in the previous step) in methanol with stirring. The reaction mixture was refluxed until all formyl group disappeared as indicated by TLC. The reaction mixture was cooled to room temperature. The precipitated product was collected by filtration and purified by recrystallization from methanol, followed by column chromatography using a mixture of ethyl acetate and hexane in a volume ratio of 1:5 as the eluent. The yield of 10-[6-(3-{2,2-diphenylhydrazone} methyl)-10H-10-phenothiazinyl]hexyl]-10H-3-phenothiazinecarbaldehyde N,N-diphenylhydrazone was 70%. The IR spectrum of the product in a KBr salt window displayed the following characteristic vibrational frequencies, $v$ ($cm^{-1}$): 3060 (ar. C—H), 2940, 2870 (alk.C—H), 1590 (C=N), 1500, 1470 (ar. C=C), and 1230 (C—N). The $^1$H-NMR spectrum (100 MHz) of the product in $CDCl_3$ was characterized by the following chemical shifts ($\delta$, ppm): 1.35–1.60 (m, 4H), 1.65–1.80 (m, 4H,), 3.80 (t, 4H), and 6.80–7.50 (m, 36H).

Compound (3)

Compound (3) can be prepared similar to Compound (2) except that phenothiazine is replaced with phenoxazine.

Compound (4)

Compound (4) can be prepared similar to Compound (2) except that phenothiazine is replaced with N-phenyl phenazine.

Compound (5)

Compound (5) was prepared similar to Compound (2) except that N-diphenylhydrazine hydrochloride was replaced with N-methyl-N-phenylhydrazine (from Aldrich Chemicals, Milwaukee, Wis.). The yield of 10-[6-(3-{2-methyl-2-phenylhydrazone}methyl)-10H-10-phenothiazinyl]hexyl]-10H-3-phenothiazine carbaldehyde N-methyl-N-phenylhydrazone was 88% The IR spectrum of the product in a KBr salt window displayed the following characteristic vibrational frequencies, $v$ ($cm^{-1}$): 3060 (ar. C—H), 2940, 2870 (alk. C—H), 1590 (C=N), 1500, 1460 (ar. C=C), and 1230 (C—N). The $^1$H NMR spectrum (250 MHz) of the product in $CDCl_3$ was characterized by the following chemical shifts ($\delta$, ppm): 1.30–1.55 (m, 4H), 1.60–1.90 (m, 4H), 3.40 (s, 6H), 3.85 (t, 4H), and 6.80–7.60 (m, 26H).

Example 2

Ionization Potential

This example provides measurements of the ionization potential for Compounds (2) and (5) synthesized as described in Example 1.

To perform the ionization potential measurements, a thin layer of the charge transport material about 0.5 µm thickness was coated from a solution of 2 mg of the charge transport material in 0.2 ml of tetrahydrofuran on a 20 cm² substrate surface. The substrate was an aluminized polyester film coated with a 0.4 µm thick methylcellulose sub-layer.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was $2-5 \cdot 10^{-8}$ W. A negative voltage of –300 V was applied to the sample substrate. A counter-electrode with the $4.5 \times 15$ mm² slit for illumination was placed at 8 mm distance from the sample surface. The counter-electrode was connected to the input of a BK2–16 type electrometer, working in the open input regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}=f(hv)$ dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography*, 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference). The linear part of this dependence was extrapolated to the hv axis and the Ip value was determined as the photon energy at the interception point. The ionization potential measurement has an error of ±0.03 eV.

The ionization potential data for Compounds (2) and (5) are listed in Table 1.

TABLE 1

| Sample | $\mu_0$ (cm²/V · s) | µ (cm²/V · s) at 6.4 · 10⁵ V/cm | α (cm/V)^0.5 | Ionization Potential (eV) |
|---|---|---|---|---|
| Sample 1/ Compound (2) | $8 \times 10^{-9}$ | $7.5 \times 10^{-7}$ | 0.0057 | 5.40 |
| Sample 2/ Compound (5) | $2.7 \cdot 10^{-9}$ | $4.1 \cdot 10^{-7}$ | 0.0063 | 5.36 |

Example 3

Charge Mobility Measurements

This example describes the measurement of charge mobility, specifically hole mobility, for charge transport materials, such as Compounds (2) and (5) as described above.

Sample 1

A mixture of 0.1 g of Compound (2) and 0.1 g of polyvinylbutyral (S-LEC B BX-1, obtained from Sekisui) was dissolved in 2 ml of tetrahydrofuran (THF). The solution was coated on a polyester film with a conductive aluminum layer by a dip roller. After the coating was dried for 1 hour at 80° C., a clear 10 µm thick layer was formed. The hole mobility of the sample was measured and the results are presented in Table 1.

Sample 2

A mixture of 0.1 g of Compound (5) and 0.1 g of polyvinylbutyral (S-LEC B BX-1, obtained from Sekisui) was dissolved in 2 ml of tetrahydrofuran (THF). The solution was coated on a polyester film with a conductive aluminum layer by a dip roller. After the coating was dried for 1 hour at 80° C., a clear 10 µm thick layer was formed. The hole mobility of the sample was measured and the results are presented in Table 1 above.

Mobility Measurements

Each sample was corona charged positively up to a surface potential U and illuminated with 2 ns long nitrogen laser light pulse. The hole mobility µ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The hole mobility measurement was repeated with changes to the charging regime to charge the sample to different U values, which corresponded to different electric field strength, E, inside the layer. This dependence on electric field strength was approximated by the formula $$\mu=\mu_0 e^{\alpha\sqrt{E}}$$

Here E is electric field strength, $\mu_0$ is the zero field mobility and α is Pool-Frenkel parameter. Table 1 lists the mobility characterizing parameters $\mu_0$ and α values and the mobility value at the $6.4 \times 10^5$ V/cm field strength as determined from these measurements.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

a) a charge transport material having the following formula:

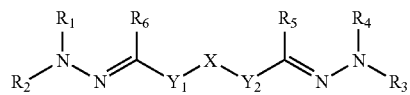

where X is a linking group;

$Y_1$ and $Y_2$ are, each independently, a phenothiazine group, a phenoxazine group, or a phenazine group;

$R_1$, $R_2$, $R_3$, and $R_4$ are, each independently, an alkyl group, an alkenyl group, a heterocyclic group, or an aromatic group; and $R_5$ and $R_6$ are, each independently, a hydrogen, an alkyl group, an alkenyl group, a heterocyclic group, or an aromatic group; and (b) a charge generating compound.

2. An organophotoreceptor according to claim 1 wherein X comprises a —(CH$_2$)$_m$— group, where in is an integer between 1 and 30, inclusive, and one or more of the methylene groups is optionally replaced by O, S, N, C, B, Si, P, C═O, O═S═O, a heterocyclic group, an aromatic group, an NR$_a$ group, a CR$_b$ group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group. a thiol group, a carboxyl group, an ammo group, an alkyl group, an alkoxy group, an alkenyl group, a heterocyclic group, an aromatic group, or part of a ring group.

3. An organophotoreceptor according to claim 1 wherein the charge transport material having the following formula:

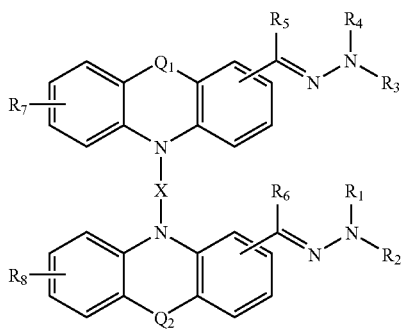

where Q$_1$ and Q$_2$ are, independently, S, O, or NR$_9$ where R$_9$ is a hydrogen, an alkyl group, an alkenyl group, a heterocyclic group, or an aromatic group;

R$_1$, R$_2$, R$_3$, and R$_4$ are, each independently, an alkyl group, an alkenyl group, a heterocyclic group, or an aromatic group;

R$_5$ and R$_6$, each independently, a hydrogen, an alkyl group, an alkenyl group, a heterocyclic group, or an aromatic group;

R$_7$ and R$_8$ are, each independently, a hydrogen, a nitro group, a cyano group, a halogen, an alkoxy group, a hydroxyl group, a thiol group, an amino group, a carboxyl group, an alkyl group, an alkenyl group, a heterocyclic group, or an aromatic group; and X is a linking group.

4. An organophotoreceptor according to claim 3 wherein X comprises a —(CH$_2$)$_m$— group, where m is an integer between 1 and 30, inclusive, and one or more of the methylene groups is optionally replaced by O, S, N, C, B, Si, P, C═O, O═S═O, a heterocyclic group, an aromatic group, an NR$_a$ group, a CR$_b$ group, a CR$_c$R$_d$s group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an ammo group, an alkyl group, an alkoxy group, an alkenyl group, a heterocyclic group, an aromatic group, or part of a ring group.

5. An organophotoreceptor according to claim 3 wherein the charge transport material comprises the following formula:

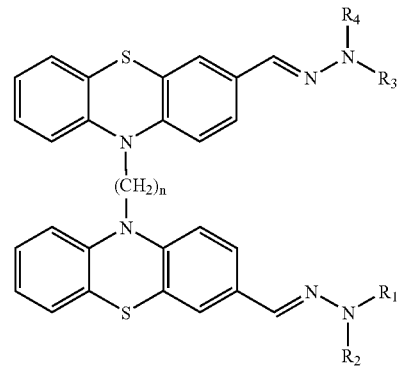

where n is an integer between 1 and 30 and R$_1$, R$_2$, R$_3$, and R$_4$ are, each independently, an alkyl group, an alkenyl group, a heterocyclic group, or an aromatic group.

6. An organophotoreceptor according to claim 5 wherein the second charge transport material comprises an electron transport compound.

7. An organophotoreceptor according to claim 1 wherein the photoconductive element further comprises a second charge transport material.

8. An organophotoreceptor according to claim 1 wherein said organophotoreceptor is in the form of a drum or a belt.

9. An organophotoreceptor according to claim 1 comprising:
   (a) a charge transport layer comprising said charge transport material and a polymeric binder; and
   (b) a charge generating layer comprising said charge generating compound and a polymeric binder.

10. An electrophotographic imaging apparatus comprising:
    (a) a light imaging component; and
    (b) an organophotoreceptor oriented to receive light from the light imaging component, the organophotoreceptor comprising an electrically conductive substrate and a photoconductive element on the electrically conductive substrate, the photoconductive element comprising:
    (i) a charge transport material having the formula

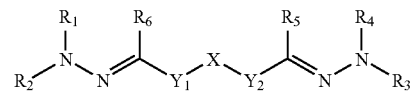

where X is a linking group;

Y$_1$ and Y$_2$ are, each independently, a phenothiazine group, a phenoxazine group, or a phenazine group;

R$_1$, R$_2$, R$_3$, and R$_4$ are, each independently, an alkyl group, an alkenyl group, a heterocyclic group, or an aromatic group; and R$_5$ and R$_6$ are, each independently, a hydrogen, an alkyl group, an alkenyl group, a heterocyclic group, or an aromatic group; and (ii) a charge generating compound.

11. An electrophotographic imaging apparatus according to claim 10 wherein X comprises a —(CH$_2$)$_m$— group, where m is an integer between 1 and 30, inclusive, and one or more of the methylene groups is optionally replaced by O, S, N, C, B, Si, P, C═O, O═S═O, a heterocyclic group, an aromatic group, an NR$_a$ group, a CR$_b$, group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

12. An electrophotographic imaging apparatus according to claim 10 wherein the charge transport material having the following formula:

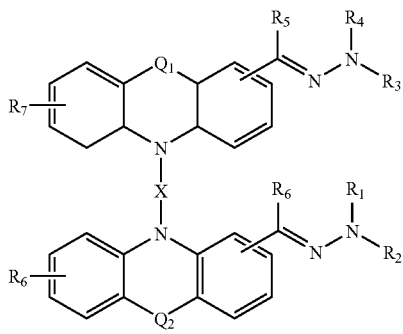

where $Q_1$ and $Q_2$ are, independently, S, O, or $NR_9$ where $R_9$ is a hydrogen, an alkyl group, an alkenyl group, a heterocyclic group, or an aromatic group;

$R_1$, $R_2$, $R_3$, and $R_4$ are, each independently, an alkyl group, an alkenyl group, a heterocyclic group, or an aromatic group;

$R_5$ and $R_6$, each independently, a hydrogen, an alkyl group, an alkenyl group, a heterocyclic group, or an aromatic group;

$R_7$ and $R_8$ are, each independently, a hydrogen, a nitro group, a cyano group, a halogen, an alkoxy group, a hydroxyl group, a thiol group, an amino group, a carboxyl group, an alkyl group, an alkenyl group, a hetero cyclic group, or an aromatic group; and X is a linking group.

13. An electrophotographic imaging apparatus according to claim 12 wherein X comprises a —(CH$_2$)$_m$— group, where m is an integer between 1 and 30, inclusive, and one or more of the methylene groups is optionally replaced by O, S, N, C, B, Si, P, C=O, O=S=O, a heterocyclic group, an aromatic group, an NR$_a$ group, a CR$_b$ group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

14. An electrophotographic imaging apparatus according to claim 12 wherein the charge transport material comprises the following formula:

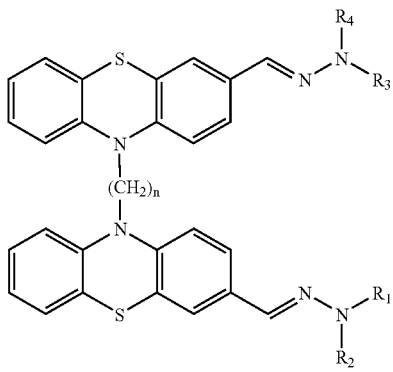

where n is an integer between 1 and 30 and $R_1$, $R_2$, $R_3$, and $R_4$ are, each independently, an alkyl group, an alkenyl group, a heterocyclic group, or an aromatic group.

15. An electrophotographic imaging apparatus according to claim 10 wherein the photoconductive element further comprises a second charge transport material.

16. An electrophotographic imaging apparatus according to claim 15 wherein the second charge transport material comprises an electron transport compound.

17. An electrophotographic imaging apparatus according to claim 10 further comprising a toner dispenser.

18. An electrophotographic imaging process comprising:
(a) applying an electrical charge to a surface of an organophotoreceptor comprising an electrically conductive substrate and a photoconductive element on the electrically conductive substrate, the photoconductive element comprising
(i) a charge transport material having the formula

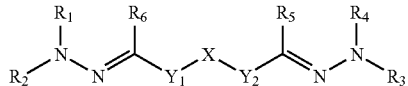

where X is a linking group;

$Y_1$, and $Y_2$ are, each independently, a phenothiazine group, a phenoxazine group, or a phenazine group;

$R_1$, $R_2$, $R_3$, and $R_4$ are, each independently, an alkyl group, an alkenyl group, a heterocyclic group, or an aromatic group; and $R_5$, and $R_6$ are, each independently, a hydrogen, an alkyl group, an alkenyl group, a heterocyclic group, or an aromatic group;

(b) imagewise exposing the surface of the organophotoreceptor to radiation to dissipate charge in selected areas and thereby form a pattern of charged and uncharged areas on the surface;

(c) contacting the surface with a toner to create a toned image; and (d) transferring the toned image to substrate.

19. An electrophotographic imaging process according to claim 18 wherein X comprises a —(CH$_2$)$_m$— group, where m is an integer between 1 and 30, inclusive, and one or more of the methylene groups is optionally replaced by O, S, N, C, B, Si, P, C=O, O=S=O, a heterocyclic group, an aromatic group, an NR$_a$ group, a CR$_b$, group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

20. An electrophotographic imaging process according to claim 18 wherein the charge transport material having the following formula:

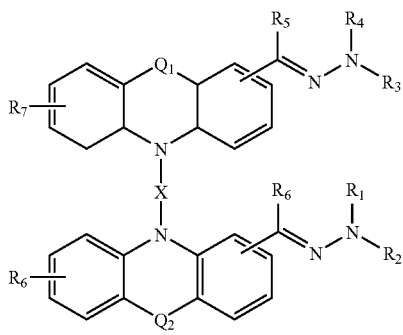

where $Q_1$ and $Q_2$ are, independently, S, O, or $NR_9$ where $R_9$ is a hydrogen, an alkyl group, an alkenyl group, a heterocyclic group, or an aromatic group;

$R_1$, $R_2$, $R_3$, and $R_4$ are, each independently, an alkyl group, an alkenyl group, a heterocyclic group, or an aromatic group;

$R_5$ and $R_6$, each independently, a hydrogen, an alkyl group, an alkenyl group, a heterocyclic group, or an aromatic group;

$R_7$ and $R_8$ are, each independently, a hydrogen, a nitro group, a cyano group, a halogen, an alkoxy group, a hydroxyl group, a thiol group, an amino group, a carboxyl group, an alkyl group, an alkenyl group, a heterocyclic group, or an aromatic group; and X is a linking group.

21. An electrophotographic imaging process according to claim 20 wherein X comprises a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$, group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

22. An electrophotographic imaging process according to claim 20 wherein the charge transport material comprises the following formula:

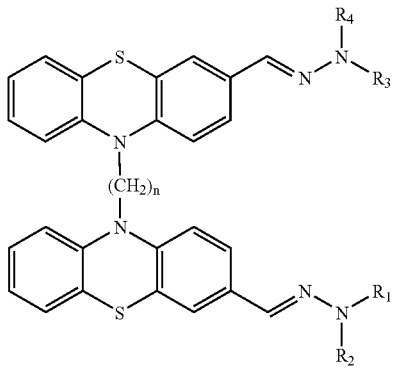

where n is an integer between 1 and 30 and $R_1$, $R_2$, $R_3$, and $R_4$ are, each independently, an alkyl group, an alkenyl group, a heterocyclic group, or an aromatic group.

23. An electrophotographic imaging process according to claim 18 wherein the photoconductive element further comprises a second charge transport material.

24. An electrophotographic imaging process according to claim 23 wherein the second charge transport material comprises an electron transport compound.

25. A charge transport material having the formula

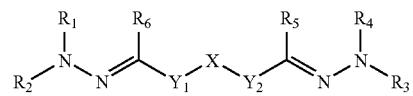

where X is a linking group;

$Y_1$ and $Y_2$ are, each independently, a phenothiazine group, a phenoxazine group, or a phenazine group;

$R_1$, $R_2$, $R_3$, and $R_4$ are, each independently, an alkyl group, an alkenyl group, a heterocyclic group, or an aromatic group; and $R_5$ and $R_6$ are, each independently, a hydrogen, an alkyl group, an alkenyl group, a heterocyclic group, or an aromatic group.

26. A charge transport material according to claim 25 wherein X comprises a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$, group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

27. A charge transport material according to claim 25 wherein the charge transport material having the following formula:

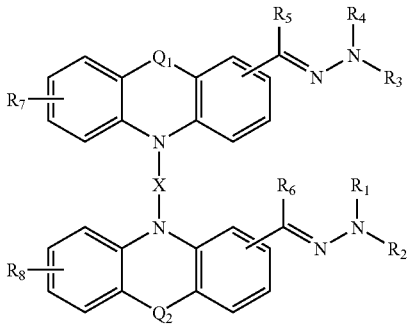

where $Q_1$ and $Q_2$ are, independently, S, O, or $NR_9$ where $R_9$ is a hydrogen, an alkyl group, an alkenyl group, a heterocyclic group, or an aromatic group;

$R_1$, $R_2$, $R_3$, and $R_4$ are, each independently, an alkyl group, an alkenyl group, a heterocyclic group, or an aromatic group;

$R_5$ and $R_6$, each independently, a hydrogen, an alkyl group, an alkenyl group, a heterocyclic group, or an aromatic group;

$R_7$ and $R_8$ are, each independently, a hydrogen, a nitro group, a cyano group, a halogen, an alkoxy group, a hydroxyl group, a thiol group, an amino group, a carboxyl group, an alkyl group, an alkenyl group, a heterocyclic group, or an aromatic group; and X is a linking group.

28. A charge transport material according to claim 27 wherein X comprises a —(CH$_2$)$_m$— group, where in is an integer between 1 and 30, inclusive, and one or more of the methylene groups is optionally replaced by O, S, N, C, B, Si, F, C=O, O=S=O, a heterocyclic group, an aromatic group, an NR$_a$ group, a CR$_b$ group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

29. A charge transport material according to claim 27 wherein the charge transport material comprises the following formula;

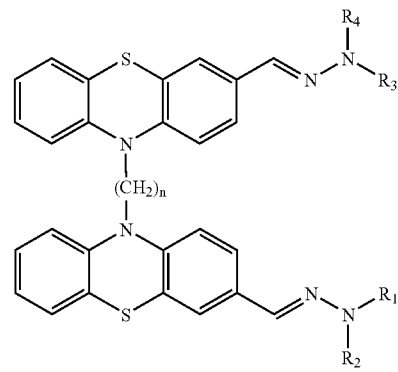

where n is an integer between 1 and 30 and R$_1$, R$_2$, R$_3$, and R$_4$ are, each independently, an alkyl group, an alkenyl group, a heterocyclic group, or an aromatic group.

* * * * *